US009329189B2

(12) United States Patent
Mercken et al.

(10) Patent No.: US 9,329,189 B2
(45) Date of Patent: May 3, 2016

(54) N-11 TRUNCATED AMYLOID-BETA Aβ11-X MONOCLONAL ANTIBODIES AND COMPOSITIONS

(75) Inventors: Marc Hubert Mercken, Turnhout (BE); Marc Maria Pierre Vandermeeren, Geel (BE)

(73) Assignee: Janssen Pharmaceutica NV, Beerse (BE)

( * ) Notice: Subject to any disclaimer, the term of this patent is extended or adjusted under 35 U.S.C. 154(b) by 463 days.

(21) Appl. No.: 10/528,928

(22) PCT Filed: Sep. 9, 2003

(86) PCT No.: PCT/EP03/10092
§ 371 (c)(1),
(2), (4) Date: Mar. 23, 2005

(87) PCT Pub. No.: WO2004/029630
PCT Pub. Date: Apr. 8, 2004

(65) Prior Publication Data
US 2006/0127954 A1 Jun. 15, 2006

(30) Foreign Application Priority Data

Sep. 27, 2002 (WO) ................ PCT/EP02/11062

(51) Int. Cl.
| | | |
|---|---|---|
| A61K 39/395 | (2006.01) |
| A61K 39/00 | (2006.01) |
| C07K 16/00 | (2006.01) |
| C12P 21/08 | (2006.01) |
| G01N 33/68 | (2006.01) |
| C07K 16/18 | (2006.01) |

(52) U.S. Cl.
CPC ............ *G01N 33/6896* (2013.01); *C07K 16/18* (2013.01); *G01N 2333/4709* (2013.01); *G01N 2800/2821* (2013.01); *G01N 2800/52* (2013.01)

(58) Field of Classification Search
CPC .............. A61K 2039/505; A61K 39/3955; A61K 47/48561; A61K 51/10; C07K 2316/96; C07K 2317/92; C07K 16/18; C07K 16/468; C07K 2317/52; C07K 2317/56; C07K 2317/565
See application file for complete search history.

(56) References Cited

U.S. PATENT DOCUMENTS 6,984,720 B1 * 1/2006 Korman et al. .......... 530/388.22

FOREIGN PATENT DOCUMENTS

| WO | WO 01/62801 A2 | 8/2001 |
| WO | WO 02/47466 | 6/2002 |

OTHER PUBLICATIONS

Walker et al .J. Neuropathol. Exp. Neurol.Jul. 1994 53: 377-383.*
Pirttila et al. J. Neurol Sci. Dec. 1, 1994; 127:90-5.*
Tekirian J. Alzheimers Dis. 2001. 3: 241-248.*
Larner. Neurobiol. Aging. 2001. 22: 343.*
Solomon et al. Proc. Natl. Acad. Sci. USA. 1996. 93: 452-455.*
Huse et al. J. Biol. Chem. 2002. 277: 16278-16284.*
International Search Report dated Feb. 1, 2004, for related International Application No. PCT/EP2003/010092.
Saido et al., "Amino- and carboxyl-terminal heterogeneity of β-amyloid peptides deposited in human brain", Neuroscience Letters, vol. 215, No. 3, pp. 173-176 (1996).
Naslund et al., "Relative Abundance of Alzheimer Aβ amyloid peptide variants in Alzheimer disease and normal aging", Proceedings of the National Academy of Sciences of the United States, vol. 91, No. 18, pp. 8378-8382 (1994).
Vassar et al., "β-Secretase Cleavage of Alzheimer's Amyloid Precursor Protein by the Transmembrane Aspartic Protease BACE", Science, vol. 286, No. 5440, pp. 735-741 (1999).
G. Gouras, et al., Generation and Regulation of β-Amyloid Peptide Variants by Neurons, Journal of Neurochemistry, 71(5):1920-1925, 1998.
T. Iwatsubo, et al., Short Communication: Full-Length Amyloid-β(1-42(43)) and Amino-Terminally Modified and Truncated Amyloid-β42(43) Deposit in Diffuse Plaques, American Journal of Pathology, 149(6):1823-1830, 1996.
J. Jarrett, et al., The Carboxy Terminus of the β Amyloid Protein Is Critical for the Seeding of Amyloid Formation: Implications for the Pathogenesis of Alzheimer's Disease, Biochemistry, 32(18):4693-4697, 1993.
G. Köhler, et al., Continuous Cultures of Fused Cells Secreting Antibody of Predefined Specificity, Nature, 256: 495-497, 1975.
G. Köhler, et al., Fusion Between Immunoglobulin-Secreting and Nonsecreting Myeloma Cell Lines, Eur. J. Immunol., 6:292-295, 1976.
R. Merrifield, Solid Phase Peptide Synthesis: I. The Synthesis of a Tetrapeptide, J.Am.Chem.Soc., 85:2149-2154, 1963.
S. Pype, et al., Characterization of Amyloid β Peptides From Brain Extracts of Transgenic Mice Overexpressing the London Mutant of Human Amyloid Precursor Protein, Journal of Neurochemistry, 84:602-609, 2003.
D. Selkoe, Alzheimer's Disease: Genes, Proteins, and Therapy, Physiological Reviews, 81(2):741-766, 2001.
M. Vandermeeren, et al., The Functional γ-Secretase Inhibitor Prevents Production of Amyloid β 1-34 in Human and Murine Cell Lines, Neuroscience Letters, 315:145-148, 2001.
R. Wang, et. al., The Profile of Soluble Amyloid β Protein in Cultured Cell Media: Detection and Quantification of Amyloid β Protein and Variants by Immunoprecipitation-Mass Spectrometry, The Journal of Biological Chemistry, 271(50):31894-31902, 1996.
Asami-Odaka et al. Long amyloid Beta-protein secreted from wild-type human neuroblastoma IMR-32 cells. Biochemistry, vol. 34, No. 32, Jan. 1, 1995, pp. 10272-10278 (XP-002973741).
Liu et al., Glu11 Site Cleavage and N-Terminally Truncated AB Production upon BACE Overexpression. Biochemistry (2002) vol. 41, pp. 3128-3136.
El Mouedden et al., Neuroscience Methods, 145 (2005), pp. 97-105.
Japanese Trial Decision dated Oct. 8, 2014; JP Patent Appl No. 2004-538886.

* cited by examiner

*Primary Examiner* — Chang-Yu Wang
(74) *Attorney, Agent, or Firm* — Hal B. Woodrow

(57) ABSTRACT

This invention relates to antibodies, including specified portions or variants, specific for at least the human Amyloid-beta 11 N-terminal site, i.e. Aβ11-x peptides. It further provides methods of making and using said antibodies, including therapeutic formulations, administration and devices.

4 Claims, 3 Drawing Sheets

Fig.1.A.
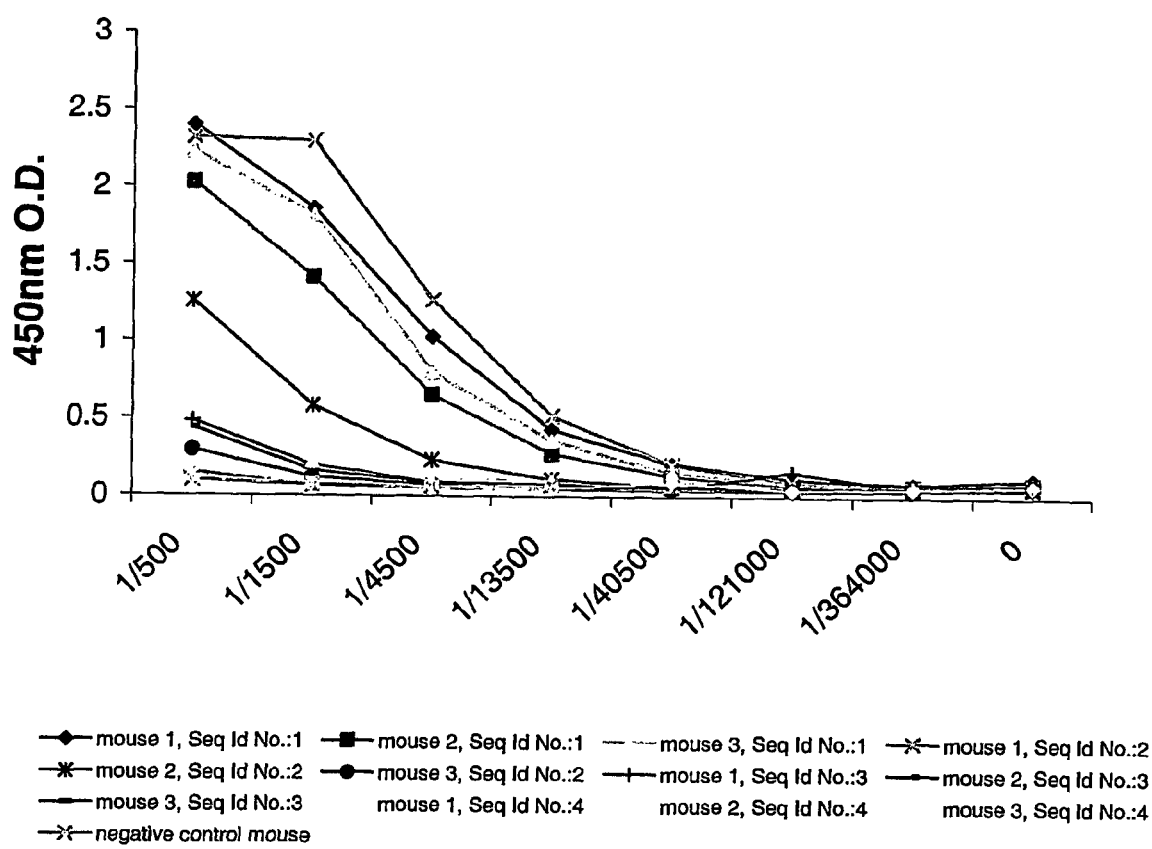

Fig2C
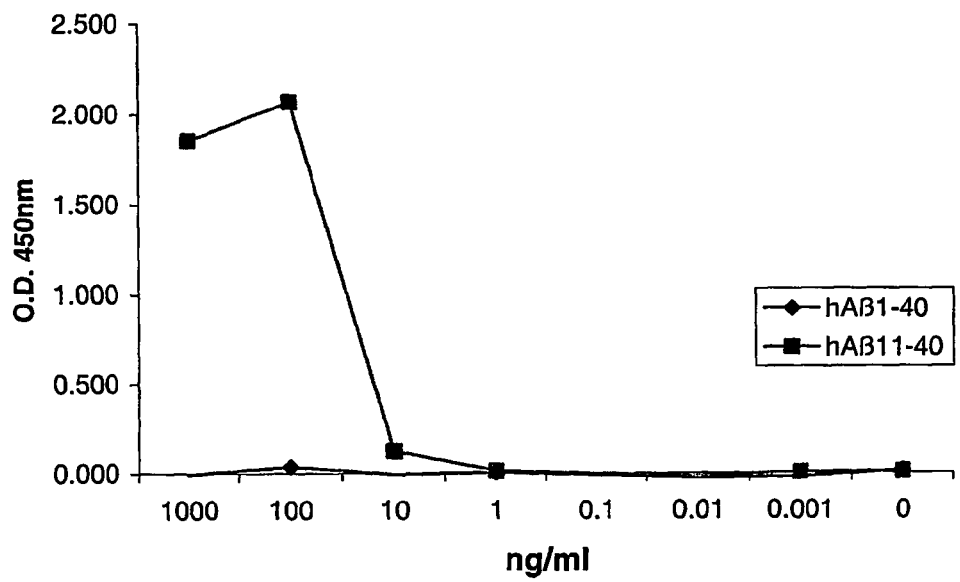
Fig 3
J&JPRD/hAβ11/1   C1/6.1
β11 stub
β1 stub
β11 stub

N-11 TRUNCATED AMYLOID-BETA Aβ11-X MONOCLONAL ANTIBODIES AND COMPOSITIONS

This application claims priority to PCT/EP03/10092, filed Sep. 9, 2003 and to PCT/EP02/11062, filed Sep. 27, 2002, the entire contents of which are incorporated herein by reference.

This invention relates to antibodies, including specified portions or variants, specific for at least the human Amyloid-beta_11 N-terminal site, i.e. Aβ11-x peptides. It further provides methods of making and using said antibodies, including therapeutic formulations, administration and devices.

BACKGROUND OF THE INVENTION

The present invention relates generally to methods and compositions for monitoring the processing of β-amyloid precursor protein. More particularly, the present invention relates to the use of such methods and compositions for the diagnosis, prognosis and monitoring response to therapy of Alzheimer's disease and other beta-amyloid related diseases as well as to the use of the disclosed antibodies in passive immunization as a method for treatment of Alzheimer's disease and other beta-amyloid related diseases.

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restricted anatomical distribution are also found in the brains of most aged humans who do not have clinical AD. Amyloid plaques and amyloid angiopathy also characterize the brains of individuals with Trisomy 21 (Down's Syndrome), Diffuse Lewy Body Disease and Hereditary Cerebral Hemorrhage with Amyloidosis of the Dutch-Type (HCHWA-D).

A major constituent of amyloid plaques are a variety amyloid-beta (Aβ) peptides which are produced by cleavage of the β-amyloid precursor protein (APP). While in the past there was significant scientific debate over whether the plaques and tangles are a cause or are merely the result of Alzheimer's disease, recent discoveries indicate that amyloid plaque is a causative precursor or factor. In particular, it has been discovered that the production of Aβ peptides can result from mutations in the gene encoding amyloid precursor protein, a protein which when normally processed will not produce the Aβ peptides. The identification of mutations in the amyloid precursor protein gene which cause familial, early onset Alzheimer's disease is the strongest evidence that amyloid metabolism is the central event in the pathogenic process underlying the disease. It is presently believed that a normal (non-pathogenic) processing of the APP protein occurs via cleavage by an "alpha.-secretase" which cleaves between amino acids 16 and 17 of the Aβ peptide region within the protein. It is further believed that pathogenic processing occurs in part via "beta.-secretases" which cleave at the amino-terminus of the Aβ peptide region within the precursor protein.

Recently, it was demonstrated that BACE-1 is the major β-secretase required for cleavage of APP at position +1 and that overexpression of BACE-1 results in an additional cleavage at the +11 site of the Aβ, generating shorter Aβ11-40 and Aβ11-42 fragments, hereinafter also referred to as the Aβ11-x peptides. These Aβ peptides have been detected in conditioned medium of primary rat neuronal cell cultures and mouse N2a cells, suggesting that they are normal APP cleavage products generated in neurons (3, 4, 5). Significantly, these shorter Aβ fragments have also been identified as major species in AD brains and normal aging brains by biochemical analysis (6) as well as in Down syndrome brains with AD pathology by immunohistochemistry studies (7). This event calls for a re-evaluation of the role of Aβ11-40/42 in the pathogenesis of Alzheimer's disease, especially in view of the fact that Aβ species beginning at Glu11 prove to be more insoluble than those beginning at position 1 of Aβ.

Despite the progress which has been made in understanding the underlying mechanisms of AD and other Aβ-related diseases, there remains a need to develop methods and compositions for diagnosis and treatment of the disease(s). Thus, the ability to monitor cellular processing of the amyloid precursor protein would be of significant value in the diagnosis, prognosis, and therapeutic supervision of Alzheimer's disease. In particular, it would be desirable to identify minimally invasive reproducible procedures for screening and evaluating detectable diagnostic markers in readily obtainable patient samples, such as serum, cerebrospinal fluid (CSF), and the like. Polyclonal antibodies such as the ones described by Said T. C., et al., Neuroscience Letters 215 (1996); 173-176 are useful to detect the different Aβ-peptides in biological samples but given the fact that each batch of polyclonal antibodies is different, these antibodies do not provide the tools to perform reproducible procedures for screening and evaluating detectable diagnostic markers in readily obtainable patient samples. In addition, the non-specific binding using polyclonal antibodies, is typically higher and the accuracy in Western blotting is typically lower.

A number of potential diagnostic markers for Alzheimer's disease have been proposed. Of particular interest to the present invention are the shorter carboxy-terminal fragments of the Aβ precursor protein obtained after beta-secretase cleavage of the APP protein. These markers should be useful by themselves and/or in combination with other diagnostic markers and procedures. Preferably, the diagnostic markers would be detectable in body fluids, such as CSF, blood, plasma, serum, urine, tissue, and the like, so that minimally invasive diagnostic procedures can be utilized.

Specific assays for Aβ11-x detection should be capable of detecting Aβ11-x in fluid samples at very low concentrations in a reproducible and consistent manner as well as distinguishing between Aβ11-x peptides and other fragments of APP, which may be present in the sample.

These and other aspects of the invention are described herein in more detail.

SUMMARY OF THE INVENTION

The present invention provides monoclonal antibodies which specifically recognize the shorter Aβ peptides obtained after cleavage of the APP protein by BACE-1 at Glu11, i.e. the Aβ-peptide fragments Aβ11-40 and Aβ11-42, hereinafter also referred to as the Aβ11-x peptides. It further provides hybridoma cells producing the monoclonal antibodies as well as methods for producing the antibodies and the hybridoma cells; and an immunoassay for an Aβ peptide by a competitive method or a sandwich method using the antibody.

In particular, the present invention provides monoclonal antibodies prepared using the first 5 to 7 human amino acids of the β-secretase_11 cleavage site, i.e. EVHHQ-C (human Aβ_11(6 AA)—Seq Id No.:1) and EVHHQKI-C (human Aβ_11(8 AA)—Seq Id No.:2) or using the first 5 to 7 mouse amino acids of the β-secretase_11 cleavage site, i.e. EVRHQ-C (mouse Aβ_11(6 AA)—Seq Id No.:3) and EVRHQKL-C (mouse Aβ_11(8 AA)—Seq Id No.:4) as immunogens. Said antibodies specifically react with the Aβ11-x peptides without cross reactivity for other APP fragments and accordingly, are useful in an immunoassay to assess the role of Aβ11-x in the pathogenesis of Alzheimer's disease.

In a more specific embodiment the monoclonal antibodies are reactive to the human Aβ_11(6 AA) immunogen and expressed by the hybridoma cells J&JPRD/hAβ11/1 and J&JPRD/hAβ11/2 deposited at the Belgian coordinated collection of microorganisms on Aug. 19, 2002 with accession numbers LMBP 5896CB and LMBP 5897CB respectively. It is thus a further embodiment of the present invention to provide the aforementioned hybridoma cells expressing the monoclonal antibodies according to the invention.

In a further aspect of the present invention the antibodies according to the invention are used in conventional immunological techniques for the detection of Aβ11-x peptides wherever it may occur, including biological samples for the monitoring of β-amyloid-related diseases and conditioned media from cell culture for monitoring the intracellular processing of APP. Suitable immunological techniques are well known to those skilled in the art and include for example, ELISA, Western Blot analysis, competitive or sandwich immunoassays and the like, as is otherwise well known they all depend on the formation of an antigen-antibody immune complex wherein for the purpose of the assay, the antibody can be detectable labeled with, e.g. radio, enzyme or fluorescent labels or it can be immobilized on insoluble carriers.

The invention also includes the use of a humanized antibody of the invention for the manufacture of a medicament, for treating, preventing or reversing Alzheimer's disease, Down's syndrome, HCHWA-D, cerebral amyloid angiopathy or other β-amyloid-related diseases; for treating, preventing or reversing cognitive decline in clinical or pre-clinical Alzheimer's disease, Down's syndrome, HCHWA-D or cerebral amyloid angiopathy; or to inhibit the formation of amyloid plaques or the effects of toxic soluble Aβ species in humans.

BRIEF DESCRIPTION OF THE DRAWING

FIG. 1 A: Serum titrations of mice injected with the first 5 to 7 human amino acids of the β-secretase_11 cleavage site, i.e. EVHHQ-C (human Ab_11(6 AA)—Seq Id No.:1) and EVHHQKI-C (β human Aβ_11(8 AA)—Seq Id No.:2) or with the first 5 to 7 mouse amino acids of the β-secretase_11 cleavage site, i.e. EVRHQ-C (β mouse Aβ_11(6 AA)—Seq Id No.:3) and EVRHQKL-C (β mouse Aβ_11(8 AA)—Seq Id No.:4) as immunogens. Coating antigen used was hAβ(11-40) (American Peptide Company) at 2.0 μg/ml.

Figure 2A:
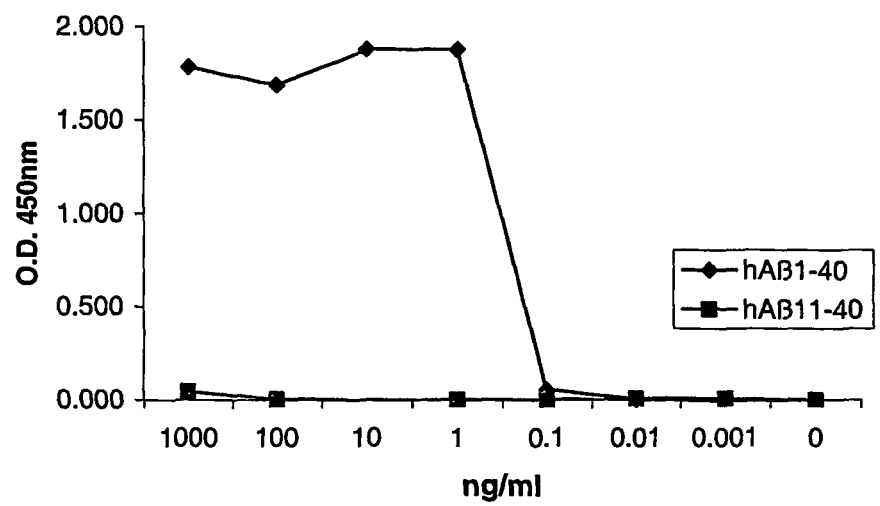

Table 1 Immunization procedure and time lines for spleen collection and fusion for mice injected with EVHHQ-C (human Aβ_11(5 AA)—Seq Id No.:1).

Table 3 Western blotting results showing specific detection of Aβ11-x peptides in brain slices of AD patients.

FIG. 2 Sandwich ELISA using purified monoclonal antibodies JRF/AβN/25, J&JPRD/hAβ11/1 and J&JPRD/hAβ11/2 as capturing antibodies and JRF/cAβ40/10-HRPO as detecting antibody. Antibody combinations are evaluated for reactivity with human Aβ1-40 and human Aβ11-40 (American Peptide Company).

A: Combination JRF/AβN/25 with JRF/cAβ40/10-HRPO reacts specifically with human Aβ1-40 without cross reaction to hAβ11-40 (positive control for Aβ1-40 detection).

B: Combination J&JPRD/hAβ11/1 with JRF/cAβ40/10-HRPO reacts specifically with hAβ11-40 without crossreaction to human Aβ1-40.

C: Combination J&JPRD/hAβ11/2 with JRF/cAβ40/10-HRPO reacts specifically with hAβ11-40 without crossreaction to human Aβ1-40.

FIG. 3 Western blotting showing specific reaction of J&JPRD/hAβ11/1 with β11-cleaved CTF fragments of APP in membrane extracts of HEK cells stably transfected with human APPswe and Human BACE1. C6/6.1 is directed to the C-terminus op APP and reacts with both β1- and β11-cleaved CTF fragments of APP.

DETAILED DESCRIPTION

The present invention provides monoclonal antibodies which specifically recognize the shorter Aβ peptides obtained after cleavage of the APP protein by BACE-1 at Glu11. The antibodies of the invention have specificity to one or more epitopes present on the first 5 to 7 amino acids of the β-secretase_11 cleavage site of human Aβ or on the first 5 to 7 amino acids of the β-secretase_11 cleavage site of mouse Aβ.

In particular, the present invention provides monoclonal antibodies prepared using peptides consisting of the first 5 to 7 human amino acids of the β-secretase_11 cleavage site, i.e. EVHHQ-C (human Aβ_11(6 AA)—Seq Id No.:1) and EVHHQKI-C (human Aβ_11(8 AA)—Seq Id No.:2) or using the first 5 to 7 mouse amino acids of the β-secretase_11 cleavage site, i.e. EVRHQ-C (mouse Aβ_11(6 AA)—Seq Id No.:3) and EVRHQKL-C (mouse Aβ_11(8 AA)—Seq Id No.:4) as immunogens.

The aforementioned peptides may be prepared produced by methods known in the art, such as the well-known Merrifield solid-phase synthesis technique where amino acids are sequentially added to a growing chain (Merrifield (1963) J. Am. Chem. Soc. 85:2149-2156). The amino acids sequences may be based on the sequence of the Aβ fragments set forth above or may utilize naturally occurring or engineered mutant sequences. For use as immunogen, the peptides thus obtained may be used by itself or may be conjugated to a suitable immunoactivating natural or synthetic carrier, such as maleimide activated serum albumin of mammals such as bovine, rabbit, and human, thyroglobulin of mammals such as bovine, rabbits, human and sheep and keyhole limpet hemocyanin (KLH) or other suitable protein carriers such as the synthetic polymer carriers including styrene polymers, acrylic polymers, vinyl polymers and propylene polymers. Further detailed descriptions of immunization can be found in the examples.

Once a sufficient amount of the immunogen has been obtained, polyclonal antibodies specific for the Aβ11-x peptides may be produced in various ways using techniques including in vitro or in vivo techniques. In vitro techniques involve exposure of lymphocytes to the immunogens, while in vivo techniques require the injection of the immunogens into a suitable vertebrate host. Suitable vertebrate hosts are non-human, including mice, rats, rabbits, sheep, goats and the like. Immunogens are injected into the animal according to a predetermined schedule, and the animals are periodically bled with successive bleeds having improved titer and specificity. The injections may be made intramuscularly, intraperitoneally, subcutaneously, or the like and an adjuvant, such as Freund's complete adjuvant or Freund's incomplete adjuvant may be given to enhance antibody producing ability. Methods for screening the serum titer levels typically include standard ELISA or RIA assays. For example in an ELISA screening format the serum is added to a solid phase (for example the bottom of a microplate) which is coated with either the Aβ11-x peptide or the Aβ11-x peptide coupled to a carrier (such as BSA), and then, adding an anti-immunoglobin antibody (for example when the immunization is performed in mice, an anti-mouse immunoglobulin antibody is used, e.g. sheep-anti-mouse immunoglobulin (Ig)) conjugated with a detectable label such as an enzyme, preferably horseradish peroxidase, or a radioactive isotope such as $^{125}I$.

If desired, monoclonal antibodies can be prepared from the vertebrate hosts, such as a mouse, hyperimmunized with the desired immunogen by the method just described, using techniques well understood by those having ordinary skill in the art. Conveniently, a vertebrate host showing a high titer antibody is selected from the animals immunized with the desired immunogen. Typically 2 to 5 days, preferably 4 days after the final immunization, the spleen or lymph nodes are collected therefrom, and antibody-producing cells contained therein immortalized. The manner of immortalization is not critical. Presently, the most common technique is fusion with a myeloma cell fusion partner. The fusing procedure can be conducted according to methods known in the art, for example, the method of Kohler and Milstein (Nature, 256, 495-497 (1975)). Other techniques include EBV transformation, transformation with bare DNA e.g. oncogenes, retroviruses, etc., or any other method which provides for stable maintenance of the cell line and production of monoclonal antibodies. Fusion accelerators, including polyethylene glycol (PEG) and Sendai virus, may be used. In particular PEG is preferably used. Examples of the myeloma cells include NS-1, P3U1, SP2/0 and AP-1, SP2/0 cells are preferably used.

Hybridomas producing monoclonal antibodies specific for epitopes which are found on the first 5 to 7 amino acids of the β-secretase_11 cleavage site of human Aβ or on the first 5 to 7 amino acids of the β-secretase_11 cleavage site of mouse Aβ are most effectively produced by first immunizing an animal from which hybridomas can be produced such as, for example a Balb/c mouse, with initial intraperitoneally injections of the desired immunogens in Freund's adjuvant, followed by booster injections every two weeks. The subsequent fusion of the isolated spleen can be carried out using any techniques commonly known to those of ordinary skill in the art, preferably using SP2/0 cells by a modified procedure of Kohler and Milstein (Eur. J. Immunol., 6, 292-295 (1976)). The screening of the hybridomas to determine which ones are producing antibodies specific for the Aβ11-x peptides can be done either in a standard ELISA or RIA assay as described hereinbefore. Selection and breeding of the hybridomas producing the desired monoclonal antibodies, is usually conducted in a medium for animals (for example Dulbecco's modified Eagle's medium (DMEM) or Eagle's minimum essential medium (MEM)) supplemented with 10-20% fetal calf serum and other components such as, for example, HAT (hypoxanthine, aminopterin and thymidine), or ESG Hybridoma supplement. Accordingly in one embodiment the present invention provides the hybridoma cells J&JPRD/hAβ11/1 and J&JPRD/hAβ11/2 deposited at the Belgian coordinated collection of microorganisms on Aug. 19, 2002 with accession numbers LMBP 5896CB and LMBP 5897CB respectively.

Separation and purification of the anti-Aβ11-x monoclonal antibodies are carried out similarly to usual separation and purification of polyclonal antibodies such as salt precipitation, alcohol precipitation, isoelectric precipitation, electrophoresis, adsorption and desorption with ion-exchange materials (for example DEAE), ultracentrifugation, gel filtration and specific immunoaffinity separation techniques including antigen-binding solid phases and protein A or protein G affinity chromatography. Suitable protein purification techniques are described in *Methods in Enzymology*, Vol. 182, Deutcher, ed., Academic Press. Inc., San Diego, 1990, the disclosure of which is incorporated herein by reference.

It is thus an object of the invention to provide isolated monoclonal antibodies expressed by the aforementioned hybridoma cells, said antibodies capable of specifically recognising Aβ11-x peptides. Preferably these isolated monoclonal antibodies are expressed by the hybridoma cells J&JPRD/hAβ11/1 and J&JPRD/hAβ11/2 deposited at the Belgian coordinated collection of microorganisms on Aug. 19, 2002 with accession numbers LMBP 5896CB and LMPB 5897CB respectively.

The antibodies according to the invention are used in conventional immunological techniques for the detection of Aβ11-x peptides wherever it may occur, including biological samples for the monitoring of β-amyloid-related diseases and conditioned media from cell culture for monitoring the intracellular processing of APP. Suitable immunological techniques are well known to those skilled in the art and include for example, ELISA, Western Blot analysis, competitive or sandwich immunoassays and the like, as is otherwise well known they all depend on the formation of an antigen-antibody immune complex wherein for the purpose of the assay, the antibody can be detectable labeled with, e.g. radio, enzyme, luminescent or fluorescent labels or it can be immobilized on insoluble carriers. It is thus an object of the invention to provide immunoassays for the determination or detection of Aβ11-x peptides in a sample, the method comprising contacting the sample with an antibody to Aβ11-x peptides according to the invention and determining whether an immune complex is formed between the antibody and the Aβ11-x peptide. These methods can either be performed on tissue samples or body fluid samples and generally comprise obtaining a sample from the body of a subject; contacting said sample with an imaging effective amount of a detectably labeled antibody according to the invention; and detecting the label to establish the presence of Aβ11-x peptides in the sample.

The measuring methods using the antibodies of the present invention are not particularly limited. Any measuring method may be used as long as the amount of antibodies, antigens or the antigens-antibody complexes corresponding to the amount of the antigens, in particular the amount of Aβ11-x peptides in solutions to be measured is detected by chemical or physical means, and calculated from standard curves prepared by the use of standard solutions containing the antigens in known amounts. For example, nephelometry, competitive methods, immunometric methods and sandwich methods are suitably used. With respect to sensitivity and specificity, it is particularly preferred to use sandwich methods described below.

In measuring methods using labelling substances, radioisotopes, enzymes, fluorescent substances, luminous substances, etc. are used as labelling agents. Examples of the radioisotopes include $^{125}I$, $^{131}I$, $^{3}H$ and $^{14}C$. Enzymes are usually made detectable by conjugation of an appropriate substrate that, in turn catalyzes a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase. Further, the avidin-biotin systems can also be used for labelling the antibodies and immunogens of the present invention.

When the immunogens or antibodies are insolubilized, either physical adsorption or chemical binding usually used for insolubilization or fixation of proteins or enzymes may be employed. Examples of the carriers include insoluble polysaccharides such as agarose, dextran, and cellulose, synthetic resins such as polystyrene, polyacrylamide and silicone polymers, and glass.

In the sandwich methods, the test solutions are reacted with the insolubilized anti-Aβ11-x peptide antibodies (the first reaction), further, the labeled anti-Aβ11-x peptide antibodies are reacted (the second reaction), and then, the activity of the labeling agents on the insolubilized carriers is assayed, whereby the amount of the Aβ11-x peptides in the test solutions can be determined. The first reaction and the second reaction may be conducted simultaneously or sequentially.

In a further embodiment for diagnosing β-amyloid-related diseases a biological sample including tissue, body fluids, such as CSF, blood, plasma, serum, urine, and the like, is contained and contacted with a suitable amount of first antibody to produce an immune complex. The contact typically involves adding the sample to a solid matrix coated with the first antibody. The complex which results from contacting the sample with the first antibody is separated from the sample by elution. However, other methods of recovery may be employed. The recovered complex is contacted with at least one second antibody directed to an antigenic determinant on the antigen and capable of binding the antigen in the complex. The antigenic determinant to which the second antibody is directed may be the same one as to which the first antibody is directed due to the multiepitopic nature of the antigenic entity. Either the first or the second antibody may be made detectable using any of the labels described above. In a preferred embodiment, the second antibody is made detectable. The presence of the detectable antibody bound to the complex consisting of antigen bound to the first and second antibody may be readily detected using art-known techniques. By comparing the results obtained in the biological sample with those obtained on a control sample, the presence of altered Aβ11-x peptide levels may be determined.

It is accordingly, an object of the present invention to provide a sandwich assay wherein the first antibody coated to a solid matrix, hereinafter referred to as the coating antibody, consists of an antibody that recognizes the Ab11-x peptides and full length Ab40 or Ab42 and the second antibody, which is made detectable, specifically recognizes the Ab11-x peptides. Preferably, the coating antibody recognizes the human Ab11-x peptides and full length human Ab40 or Ab42, in a more preferred embodiment the coating antibody consists of the monoclonal antibody JRF/cAb40/10 that specifically recognizes Ab11-40 and full length Ab40, said monoclonal antibody being characterised by comprising at least one heavy chain variable region heaving the amino acid sequence of SEQ ID No:5 and/or at least one light chain variable region having the amino acid sequence of SEQ ID No:6 (hereinafter referred to as the monoclonal antibody JRF/cAb40/10) or alternatively, the coating antibody consists of the monoclonal antibody JRF/cAb42/12 that specifically recognizes Ab11-42 and full length Ab42, said monoclonal antibody being characterised by comprising at least one heavy chain variable region heaving the amino acid sequence of SEQ ID No:7 and/or at least one light chain variable region having the amino acid sequence of SEQ ID No:8 (hereinafter referred to as the monoclonal antibody JRF/cAb42/12). Accordingly in a preferred embodiment the second antibody is one of the monoclonal antibodies expressed by the hybridoma cells J&JPRD/hAb11/1 or J&JPRD/hAb11/2 deposited at Belgian Coordinated Collections of Microorganisms (BCCM), Prime Minister's Services, Federal Office for Scientific, Technical and Cultural Affairs (OSTC), Rue de la Science 8, B-1000 Brussels, Belgium on Aug. 19, 2002 with accession numbers LMBP 5896CB and LMBP 5897CB respectively. It is also an object of the invention to provide a sandwich assay to determine the ratio of Ab11-x peptides to full length Ab40 or Ab42. In this embodiment an additional second antibody that recognizes both full length Ab40 and Ab42, but which shows no cross reactivity for Ab11-x peptides is used as well. Preferably this additional second antibody consists of JRF/AbN25 characterised by comprising at least one heavy chain variable region heaving the amino acid sequence of SEQ ID No: 9 and for at least one light chain variable region having the amino acid sequence of SEQ ID No: 10. It is accordingly an object of the present invention to provide a sandwich assay wherein the coating antibody consists of an antibody that specifically recognizes the Ab11-x peptides, but which shows no cross reactivity for the full length Ab40 and Ab42 peptides, such as for example the monoclonal antibodies expressed by the hybridoma cells J&JPRD/hAb11/1 or J&JPRD/hAb11/2 deposited at the Belgian coordinated collection of microorganisms on Aug. 19, 2002 with accession numbers LMBP 5896CB and LMBP 5897CB respectively, in combination with a second antibody that specifically recognized Ab11-40 or Ab11-42, such as for example JRF/cAb42/12 or JRF/cAb40/10 as characterized hereinbefore. In a specific embodiment the coating antibody consists of J&JPRD/hAb11/1 and the second antibody consists of JRF/cAb42/26 that specifically recognizes Ab11-42 and full length Ab42, said monoclonal antibody being characterised by comprising at least one heavy chain variable region heaving the amino acid sequence of SEQ ID No:11 and for at least one light chain variable region having the amino acid sequence of SEQ ID No:12 (hereinafter referred to as the monoclonal antibody JRF/cAb42/26).

In an alternative sandwich assay to determine the ratio of Aβ11-x peptides to full length Aβ40 or Aβ42, the coating antibody consists of an antibody that specifically recognizes the Aβ11-x peptides, preferably the human Aβ11-x peptides and the second antibody, which is made detectable, specifically recognizes the peptides Aβ11-40 or Aβ11-42, preferably human Aβ11-40 or human Aβ11-42. In this alternative sandwich assay the coating antibody consists of one of the monoclonal antibodies expressed by the hybridoma cells J&JPRD/hAβ11/1 or J&JPRD/hAβ11/2 deposited at the Belgian coordinated collection of microorganisms on Aug. 19, 2002 with accession numbers LMBP 5896CB and LMBP 5897CB respectively, and the second, detectably labeled antibody consist of either the monoclonal antibody JRF/cAβ40/10 or the monoclonal antibody JRF/cAβ42/12 as characterized hereinbefore.

The monoclonal antibodies of the present invention can also be used in assay systems other than the sandwich methods, for example, competitive methods and nephelometry. In the competitive methods, antigens in test solutions and labeled immunogens are competitively reacted with the antibodies, followed by separation of the unreacted labeled immunogens (F) from the labeled immunogens (B) bound to the antibodies (B/F separation). Then, the labeled amount of either B or F is measured to determine the amount of immunogen in the test solution. These reaction methods include liquid phase methods in which soluble antibodies are used as the antibodies and polyethylene glycol and the second antibodies to the above mentioned antibodies are used for B/F separation, and solidifying methods in which solidified antibodies are used as the first antibodies, or soluble antibodies are used as the first antibodies and solidified antibodies are used as the second antibodies.

In nephelometry, the amount of the insoluble precipitates produced as a result of antibody-antigen reaction in gels or solutions is measured. Even when the amount of antigens is slight, and the precipitates are obtained only in small amounts, laser nephelometry using laser scattering is suitably used.

In a further aspect, the invention is directed to a method to treat and to prevent conditions characterized by the formation of plaques containing beta-amyloid protein in humans, which method comprises administering, preferably peripherally, to a human in need of such treatment a therapeutically or prophylactically effective amount of humanized monoclonal antibody according to the invention or immunologically reactive fragment thereof, which antibody specifically binds to one or more epitopes present on the first 5 to 7 amino acids of the β-secretase_11 cleavage site of human or mouse Aβ peptide. In another aspect, the invention is directed to a method to inhibit the formation of amyloid plaques and to clear amyloid plaques in humans, which method comprises administering to a human subject in need of such inhibition an effective amount of a humanized antibody that sequesters Aβ peptide from its circulating form in blood and induces efflux out of the brain as well as altered Aβ clearance in plasma and the brain. In additional aspects, the invention is directed to such humanized antibodies, including immunologically effective portions thereof, and to methods for their preparation.

By "humanized antibody" is meant an antibody that is composed partially or fully of amino acid sequences derived from a human antibody germline by altering the sequence of an antibody having non-human complementarity determining regions (CDR). "CDRs" are defined as the complementarity determining region amino acid sequences of an antibody which are the hypervariable regions of immunoglobulin heavy and light chains. See, e.g. Kabat et al., *Sequences of proteins of immunological interest, 4$^{th}$* Ed., U.S. Department of Health and Human Services, National Institutes of Health (1987). There are three heavy chain and three light chain CDRs (or CDR regions) in the variable portion of an immunoglobulin. Thus "CDRs" as used herein refers to all three heavy chain CDRs or all three light chain CDRs (or both light and heavy chain CDRs, if appropriate).

The simplest such alteration may consist simply of substituting the constant region of a human antibody for the murine constant region, thus resulting in a human/murine chimera which may have sufficiently low immunogenicity to be acceptable for pharmaceutical use.

Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. Fully human antibodies are produced in genetically modified mice whose immune systems have been altered to correspond to human immune systems. As mentioned above, it is sufficient for use in the methods of the invention, to employ an immunologically specific fragment of the antibody, including fragments representing single chain forms.

A humanized antibody again refers to an antibody comprising a human framework, at least one CDR from a non-human antibody, and in which any constant region present is substantially identical to a human immunoglobulin constant region, i.e., at least about 85 90%, preferably at least 95% identical. Hence, all parts of a humanized antibody, except possibly the CDRs, are substantially identical to corresponding parts of one or more native human immunoglobulin sequences. For example, a humanized immunoglobulin would typically not encompass a chimeric mouse variable region/human constant region antibody.

Humanized antibodies have at least three potential advantages over non-human and chimeric antibodies for use in human therapy:

1) because the effector portion is human, it may interact better with the other parts of the human immune system (e.g., destroy the target cells more efficiently by complement-dependent cytotoxicity (CDC) or antibody-dependent cellular cytotoxicity (ADCC)).

2) The human immune system should not recognize the framework or C region of the humanized antibody as foreign, and therefore the antibody response against such an injected antibody should be less than against a totally foreign non-human antibody or a partially foreign chimeric antibody.

3) Injected non-human antibodies have been reported to have a half-life in the human circulation much shorter than the half-life of human antibodies. Injected humanized antibodies will have a half-life essentially identical to naturally occurring human antibodies, allowing smaller and less frequent doses to be given.

In a method to treat and to prevent conditions characterized by the formation of plaques containing beta-amyloid protein, the antibodies (including immunologically reactive fragments) are administered to a subject at risk for or exhibiting Aβ-related symptoms or pathology such as clinical or pre clinical Alzheimer's disease, Down's syndrome, or clinical or pre-clinical amyloid angiopathy, using standard administration techniques, preferably peripherally (i.e. not by administration into the central nervous system) by intravenous, intraperitoneal, subcutaneous, pulmonary, transdermal, intramuscular, intranasal, buccal, sublingual, or suppository administration. Although the antibodies may be administered directly into the ventricular system, spinal fluid, or brain parenchyma, and techniques for addressing these locations are well known in the art, it is not necessary to utilize these more difficult procedures. The antibodies of the invention are effective when administered by the more simple techniques that rely on the peripheral circulation system. The advantages of the present invention include the ability of the antibody exert its beneficial effects even though not provided directly to the central nervous system itself. Indeed, it has been demonstrated herein that the amount of antibody which crosses the blood-brain barrier is <0.1% of plasma levels and that the antibodies of the invention exert their ability to sequester Aβ in the peripheral circulation as well as to alter CNS and plasma soluble Aβ clearance.

The pharmaceutical compositions for administration are designed to be appropriate for the selected mode of administration, and pharmaceutically acceptable excipients such as dispersing agents, buffers, surfactants, preservatives, solubilizing agents, isotonicity agents, stabilizing agents and the like are used as appropriate. Remington's Pharmaceutical Sciences, Mack Publishing Co., Easton Pa., latest edition, incorporated herein by reference, provides a compendium of formulation techniques as are generally known to practitioners.

It may be particularly useful to alter the solubility characteristics of the antibodies of the invention, making them more lipophilic, for example, by encapsulating them in liposomes or by blocking polar groups.

Peripheral systemic delivery by intravenous or intraperitoneal or subcutaneous injection is preferred. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl) propyl-N,N,N-trimethylammoniumchloride (DOTMA) or various compounds such as cholesterol hemisuccinate, phosphatidyl glycerols and the like.

The concentration of the humanized antibody in formulations from as low as about 0.1% to as much as 15 or 20% by weight and will be selected primarily based on fluid volumes, viscosities, and so forth, in accordance with the particular mode of administration selected. Thus, a typical pharmaceutical composition for injection could be made up to contain 1 mL sterile buffered water of phosphate buffered saline and 1-100 mg of the humanized antibody of the present invention. The formulation could be sterile filtered after making the formulation, or otherwise made microbiologically acceptable. A typical composition for intravenous infusion could have a volume as much as 250 mL of fluid, such as sterile Ringer's solution, and 1-100 mg per mL, or more in antibody concentration.

Therapeutic agents of the invention can be frozen or Lyophilized for storage and reconstituted in a suitable sterile carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate. The pH of the formulation will be selected to balance antibody stability (chemical and physical) and comfort to the patient when administered.

Generally, pH between 4 and 8 is tolerated.

Although the foregoing methods appear the most convenient and most appropriate for administration of proteins such as humanized antibodies, by suitable adaptation, other techniques for administration, such as transdermal administration and oral administration may be employed provided proper formulation is designed.

In addition, it may be desirable to employ controlled release formulations using biodegradable films and matrices, or osmotic mini-pumps, or delivery systems based on dextran beads, alginate, or collagen.

In summary, formulations are available for administering the antibodies of the invention and are well-known in the art and may be chosen from a variety of options. Typical dosage levels can be optimized using standard clinical techniques and will be dependent on the mode of administration and the condition of the patient.

The present invention further provides kits that can be used in the above mentioned methods. In one embodiment, a kit comprises an antibody of the invention, preferably a purified antibody, more preferably a monoclonal antibody, even more preferably the isolated monoclonal antibodies expressed by the hybridoma cells J&JPRD/hAβ11/1 and J&JPRD/hAβ11/2 deposited at the Belgian coordinated collection of microorganisms on Aug. 19, 2002 with accession numbers LMBP 5896CB and LMBP 5897CB respectively, in one or more containers. In a specific embodiment, the kits of the present invention contain a substantially isolated polypeptide comprising an epitope which is specifically immunoreactive with an antibody included in the kit. In a further embodiment this epitope is being selected from the group consisting of the first 5 to 7 human amino acids of the β-secretase_11 cleavage site, i.e. EVHHQ-C (human Aβ_11(6 AA)—Seq Id No.:1) and EVHHQKI-C (human Aβ_11(8 AA)—Seq Id No.:2) or of the first 5 to 7 mouse amino acids of the β-secretase_11 cleavage site, i.e. EVRHQ-C (mouse Aβ_11(6 AA)—Seq Id No.:3) and EVRHQKL-C (mouse Aβ_11(8 AA)—Seq Id No.:4) as immunogens. Preferably, the kits of the present invention are used in a sandwich assay and further comprise a coating antibody which does not specifically react with the polypeptide of interest, in a specific embodiment this coating antibody recognizes the Aβ11-x peptides and full length Aβ40 or Aβ42, preferably this coating antibody recognizes the human Aβ11-x peptides and full length human Aβ40 or Aβ42, in a more preferred embodiment the coating antibody consists of the monoclonal antibody JRF/cAβ40/10 (as characterized hereinbefore) that specifically recognizes Aβ11-40 and full length Aβ40 or the coating antibody consists of the monoclonal antibody JRF/cAβ42/12 (as characterized hereinbefore) that specifically recognizes Aβ11-42 and full length Aβ42. In alternative sandwich assay according to the invention, the kits will comprise a coating antibody that specifically recognizes the Aβ11-x peptides, preferably the human Aβ11-x peptides, and further antibodies specific for the C-terminus of Aβ40 or Aβ42, preferably for the C-terminus of human Aβ40 or Aβ42. In a more preferred embodiment the kit will comprise the isolated monoclonal antibodies expressed by the hybridoma cells J&JPRD/hAβ11/1 and J&JPRD/hAβ11/2 deposited at the Belgian coordinated collection of microorganisms on Aug. 19, 2002 with accession-numbers LMBP 5896CB and LMBP 5897CB respectively, as coating antibodies, and the monoclonal antibodies JRF/cAβ40/10 (as characterized hereinbefore) and the monoclonal antibody JRF/cAβ42/12 (as characterized hereinbefore) as further antibodies, the latter being conjugated to a detectable label, substrate.

In another specific embodiment, the kits of the present invention contain means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In particular the kit contains means to detect the binding of an antibody to Aβ11-x peptides, preferably to detect binding with an epitope being selected from the group consisting of the first 5 to 7 human amino acids of the β-secretase_11 cleavage site, i.e. EVHHQ-C (human Aβ_11(6 AA)—Seq Id No.:1) and EVHHQKI-C (human Aβ_11(8 AA)—Seq Id No.:2) or of the first 5 to 7 mouse amino acids of the β-secretase_11 cleavage site, i.e. EVRHQ-C (mouse Aβ_11(6 AA)—Seq Id No.:3) and EVRHQKL-C (mouse Aβ_11(8 AA)—Seq Id No.:4). In the aforementioned sandwich assays, the antibody conjugated to a detectable substrate will not be the coating antibody.

In an additional embodiment, the invention includes a diagnostic kit for use in screening biological samples including tissue, body fluids, such as CSF, blood, plasma, serum, urine, and the like. Said biological sample containing Ab11-x peptides. The diagnostic kit includes a substantially isolated antibody specifically immunoreactive with Ab11-x peptides, in particular with an epitope being selected from the group consisting of the first 5 to 7 human amino acids of the β-secretase_11 cleavage site, i.e. EVHHQ-C (human Aβ_11(6 AA)—Seq Id No.:1) and EVHHQKI-C (human Aβ_11(8 AA)—Seq Id No.:2) or of the first 5 to 7 mouse amino acids of the β-secretase_11 cleavage site, i.e. EVRHQ-C (mouse Aβ_11(6 AA)—Seq Id No.:3) and EVRHQKL-C (mouse Aβ_11(8 AA)—Seq Id No.:4), and means for detecting the binding of the antibody to the immunogen. In one embodiment, the antibody is attached to a solid support. In a specific embodiment, the antibody may be a monoclonal antibody, in particular the monoclonal antibodies expressed by the hybridoma cells J&JPRD/hAβ11/1 and J&JPRD/hAβ11/2 deposited at the Belgian coordinated collection of microorganisms on Aug. 19, 2002 with accessionnumbers LMBP 5896CB and LMBP 5897CB respectively.

The detecting means of the kit may include a second, labeled monoclonal antibody, preferably this second labeled antibody consists of JRF/cAβ40/10 or JRF/cAβ42/12 wherein the combination of the aforementioned immobilized monoclonal antibodies with JRF/cAβ40/10 specifically recognizes Aβ11-40 without cross reaction with Aβ1-40 and wherein the combination of the aforementioned immobilized monoclonal antibodies with JRF/cAβ42/12 specifically recognizes Aβ11-42 without cross reaction with Aβ1-42. Alternatively, or in addition, the detecting means may include a labeled, competing antigen.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound antibodies according to the invention, and a reporter-labeled antibody for detecting the binding of the antibody to the immunogen.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXPERIMENTAL

Material and Methods

Generation of Monoclonal Antibodies

Balb/c mice were primed with four different peptides in complete Freund's adjuvant. The first two synthetic peptides comprised the first 5 to 7 human amino acids (AA) at the β-secretase_11 cleavage site: EVHHQ-C (human Aβ_11(6 AA)—Seq Id No.:1) and EVHHQKI-C (human aβ_11(8 AA). The other two peptides for immunization contained a mouse Aβ_11 AA sequence; EVRHQ-C (mouse Aβ_11(6 AA)—Seq Id No.:3) and EVRHQKL-C (mouse Aβ_11(8 AA)—Seq Id No.:4). All the peptides were prepared by coupling the peptides via a COOH-terminal cystein residue to maleimide activated mc (*Megathura crenulata*) KLH, or to Maleimide Activated Bovine Serum Albumin, using commercially available kits such as the Imject Maleimide Activated mcKLH/BSA kit of Pierce, according to the manufacturer's instructions (Pierce, Rockford, Ill.). Mice were boosted every two weeks with 100 µg KLH-coupled peptide, first in Complete and subsequently in Incomplete Freund's adjuvant.

The spleens of all mice were isolated and frozen in liquid nitrogen except for one spleen of a mouse immunised with human Aβ_11 (6AA) peptide. The mouse selected showed the highest serum titer and was therefore selected for fusion. On day 4 before fusion or spleen extraction, all mice were boosted intraperitoneally with 100 µg of Aβ_11 peptides coupled to mcKLH in saline. Mouse spleen cells were fused with SP2/0 cells by a modified procedure of Kohler and Milstein (8). The hybridoma's were seeded in 30×96-well plates and screened after 10 days in a direct ELISA on BSA-coupled hAβ_11 peptide of 6 AA and confirmed on non-coupled Aβ11-40 peptide. Positive cells on free hAβ_11-40 were immediately subcloned and positive clones were frozen in liquid nitrogen.

All hybridoma's were grown in Dulbecco's modified Eagle's medium supplemented with 10% foetal calf serum (Hyclone, Europe), 2.5% ESG Hybridoma supplement (Elscolab, Kruibeke, Belgium), 2% HT (Sigma, USA), 1 mM sodium pyruvate, 2 mM L-glutamine and penicillin (100 U/ml) and Streptomycin (50 mg/ml). All products were commercially available and purchased from Life-Technologies (Paisley, U.K.). Cells were incubated in a humidified 8% CO2 air incubator.

ELISA Antibody Selection

The screening ELISA used for the detection of anti-Aβ_11 antibodies was a direct ELISA with 1 µg/ml free human/mouse Aβ11-40 or BSA coupled human/mouse Aβ_11 peptide coated overnight at 4° C. in NUNC (Life Technologies) U-bottom high-binding 96-well microtiter plates in 50 µl/well coating buffer (10 mM Tris, 10 mM NaCl, and 10 mM NaN3, pH 8.5). The next day, the plates were coated with 85 µl/well of 0.1% casein in PBS for 60 min at 37° C. to reduce non-specific binding. Next, 50 µl hybridoma supernatant was added and incubated for 1 h at 37° C. After washing, the bound monoclonal antibodies were detected with 50 µl/well of Sheep-anti-mouse Ig conjugated with horseradish peroxidase for 1 hr at 37° C. (Amersham-Pharmacia Biotech). Both reagents were diluted in 0.1% Casein/PBS. The plates were washed and 50 µl of a solution of 0.42 mM 3,5,3',5'-tetramethyl-benzidine, 0.003% (vol/vol) H2O2 in 100 mM citric acid and 100 mM disodium hydrogen phosphate (pH 4.3) was added as the substrate. The reaction was allowed to proceed for maximum 15 min on a plate shaker at room temperature, after which the colour development was stopped with 2 N H$_2$SO$_4$, 50 µl/well and the plates, were read on a microtiter plate reader at 450 nm (Thermomax, Molecular Devices). The cross-reactivity of the selected monoclonal antibodies with full-size human free Aβ1-40 peptide was tested in a direct ELISA, identical to the screening assay, except that full-size free human Aβ1-40 peptide was used instead of BSA coupled hAβ_11 (6AA) peptide. In a second confirmation ELISA, the selected positive cultures were re-tested on free human Aβ11-40 peptide.

Sandwich ELISA for Amyloid β Detection

The ELISA for the measurement of hAβ(1-40) or hAβ(11-40) standard dilutions (American Peptide Company) was performed as follows: Briefly, monoclonal antibodies JRF/AβN/25, J&JPRD/hAβ11/1 and J&JPRD/hAβ11/2 were coated at 5 µg/ml overnight at 4° C. in NUNC flat-bottom high-binding 96-well microtiter plates in 100 μl/well coating buffer. The next day, plates were overcoated with 125 μl/well of 0.1% casein in PBS for 30 min at 37° C. to reduce non-specific binding and incubated with 100 μl/well of hAβ(1-40) or hAβ (11-40) peptide dilution samples for 90 min at 37° C. The plates were washed followed by an incubation with 100 μl/well of HRP-labeled JRF/cAβ40/10-HRPO. The plates were washed and 100 μl of a solution of 0.42 mM 3,5,3',5'-tetramethyl-benzidine, 0.003% (vol/vol) H2O2 in 100 mM citric acid and 100 mM disodium hydrogen phosphate (pH 4.3) was added as the substrate. The reaction was allowed to proceed for maximum 15 min on a plate shaker at RT, after which the color development was stopped with 2 N H2SO4, 50 μl/well and the plates were read on a microtiter plate reader at 450 nm (Thermomax, Molecular Dynamics).

Immunodetection of APP CTF.

For immunodetection of CTF (STUBS) fragments, HEK cells, stably transfected with Human APPswe and Human BACE1, were grown in 75 cm$^2$ flasks (Life Technologies, Paisly, UK) until confluence and cells were subsequently lysed and sonicated in 50 mM Tris: pH=7.0, 0.15 M NaCl, 1% Triton X-100 and a commercially available Protease-Inhibitor-Cocktail (Roche, Boehringer Mannheim, Germany). Crude lysates were centrifuged at 10 000 g at 4° C. for 10 min to remove nuclei and debris. Cleared cell lysates were normalized for protein content and samples were denatured at 95° C. in 2× Tricine Laemmli buffer for 5 min and loaded onto precast 10-20% Tris Tricine SDS gradient gels (NOVEX, Invitrogen, Groningen, The Netherlands) and semi-dry blotted to 0.22 μm Hybond-ECL nylon membranes (APB) for 45 min at 1.5 mA per cm$^2$. A low molecular weight protein ladder was used as molecular weight standard (MagicMark Western standard, Invitrogen). The membranes were blocked with 10% (w/v) non-fat dry milk (BioRad) in PBS for 1 hour. Next they were incubated with the appropriate monoclonal antibody at 5 μg/ml overnight at 4° C. (monoclonal antibody Cl/6.1 directed against a C-terminal epitope in APP, was a generous gift of Dr. Mathews, Nathan S. Kline Institute, Orangeburg). The membranes were then washed in PBS-0.1% Tween20 for 5 min with five changes of buffer, incubated for 1 h with a HRP-conjugated goat anti-mouse (Sigma) 1:2000 dilution for 1 h at room temperature (RT). After washing, the bands of interest were visualised by chemiluminescence according to the manufacturer's instructions (Roche, Boehringer Mannheim, Germany). Scans were taken with a Lumi-Imager (Roche, Boehringer Mannheim, Germany).

Immunodetection of APP in Brain Slices of AD Patients.

The brain slices were blocked with 10% (w/v) non-fat dry milk (BioRad) in PBS for 1 hour. Next they were incubated with the appropriate monoclonal antibody at 5 μg/ml overnight at 4° C. The membranes were then washed in PBS-0.1% Tween20 for 5 min with five changes of buffer, incubated for 1 h with a HRP-conjugated goat anti-mouse (Sigma) 1:2000 dilution for 1 h at room temperature (RT). After washing, the bands of interest were visualised by chemiluminescence according to the manufacturer's instructions (Roche, Boehringer Mannheim, Germany). Scans were taken with a Lumi-Imager (Roche, Boehringer Mannheim, Germany).

Results and Discussion

Selection of the "Fusion Mouse"

A panel of 4 different mcKLH coupled peptides was injected in mice. For each peptide, 3 different mice were immunized. After the first boost immunisation, each mouse was bled and serum was isolated and tested in directly coated BSA-humanAβ (6AA) ELISA's. The immunisation protocol of mice immunised with hAβ_11(6AA) was identical for all mice injected and is shown in table 1. In FIG. 1.a, it is clearly demonstrated that mouse 1 immunised with KLH_hAβ_11 (6AA) (SEQ ID No: 1) shows a very high serum titer for free human Aβ11-40 peptide. For this reason, mouse 1 immunised with hAβ_11 (6AA) was selected for fusion Fusion of hAβ_11 (6aa), Spleen 1

Due to the large number of spleen cells of this hyper immunised mouse (a total of 6.5×10$^8$ spleen cells), the fusion procedure was performed twice with half of the spleen cell number. All cells were seeded in medium supplemented with ESG and 30×96 hybridoma plates were screened after 10 days.

Out of these hybridomas, 65 culture wells initially showed a clear positive signal in the screening ELISA assay on BSA-coupled peptide. All these positive supernatant were tested on free peptide in an IgG specific ELISA. Only 5 cultures were confirmed positive or less than 10% of the initial positive wells. All these cultures were negative on full-length human Aβ1-40, indicating reactivity to the end-standing AA of hAβ11-40/42.

The cultures were immediately cloned and the mother cultures were frozen. Out of these 5, 2 hybridoma's named 29B5 (J&JPRD/hAβ11/1) and 5C4 (J&JPRD/hAβ11/2) were successfully cloned and frozen in liquid Nitrogen. Of these two hybridoma's 4 different subclones each were cultured and frozen. In table 2, the positive subclones are summarised.

TABLE 2

| J&JPRD/hAβ11/1 (29B5cl1F3) | J&JPRD/hAβ11/2 (5C4cI3D6) |
| J&JPRD/hAβ11/1 (29B5cI2F5) | J&JPRD/hAβ11/2 (5C4cI3F5) |
| J&JPRD/hAβ11/1 (29B5cI4C1) | J&JPRD/hAβ11/2 (5C4cI5B4) |
| J&JPRD/hAβ11/1 (29B5cI4D11) | |

Determination of Aβ1-40/42 and the Truncated Aβ11-40 in CSF Samples of Non-AD Human Controls, Beagle Dogs and Guinea Pigs.

The ELISA for the measurement of Aβ1-40/42 and the truncated Aβ11-40 in CSF samples was performed as follows: Briefly, monoclonal antibodies J&JPRD/hAβ11/1 or the specific Aβx-40 and Aβx-42 monoclonal antibodies (Vandermeeren M., et al. 2001; Pype S., et al. 2003) JRF/cAβ40/10 and JRF/cAβ42/26 were coated at 5 μg/ml overnight at 4° C. in NUNC flat-bottom high-binding 96-well microtiter plates in 100 μl/well coating buffer. The next day, plates were overcoated with 150 μl/well of 0.1% casein in PBS for 30 min at 37° C. to reduce non-specific binding and incubated with 100 μl/well of PBS buffer diluted CSF samples for 90 min at 37° C. The plates were washed followed by an incubation with 100 μl/well of HRP-labeled JRF/AβN/25-HRPO or JRF/cAβ40/28-HRPO. The plates were washed and 100 μl of a solution of 0.42 mM 3,5,3',5'-tetramethyl-benzidine, 0.003% (vol/vol) H$_2$O$_2$ in 100 mM citric acid and 100 mM disodium hydrogen phosphate (pH 4.3) was added as the substrate. The reaction was allowed to proceed for maximum 15 min on a plate shaker at RT, after which the color development was stopped with 2 N H$_2$SO$_4$, 50 μl/well and the plates were read on a microtiter plate reader at 450 nm (Thermomax, Molecular Dynamics).

Using the monoclonal antibodies according to the present invention the truncated 11-40 beta-amyloid isoform could be quantitatively detected (ng/ml±stdev) in CSF samples (n=6) of non-AD human controls, Beagle dogs and Guinea pigs.

|  | human ng/ml | dog ng/ml | guinea pig ng/ml |
|---|---|---|---|
| Abeta 1–40 | 5.70 ± 0.63 | 5.61 ± 0.35 | 5.94 ± 0.42 |
| Abeta 11–40 | 0.20 ± 0.04 | 0.30 ± 0.34 | 0.36 ± 0.05 |
| Abeta 1–42 | 0.92 ± 0.31 | 1.25 ± 0.05 | 1.17 ± 0.16 |

CONCLUSION

Out of a total of more than 30.000 hybridomas, we selected two different hybridoma clones that recognise specifically the free N-terminus of the human Aβ11-40 peptide. These monoclonal antibodies are negative on full size human Aβ1-40.

Figure 2B:
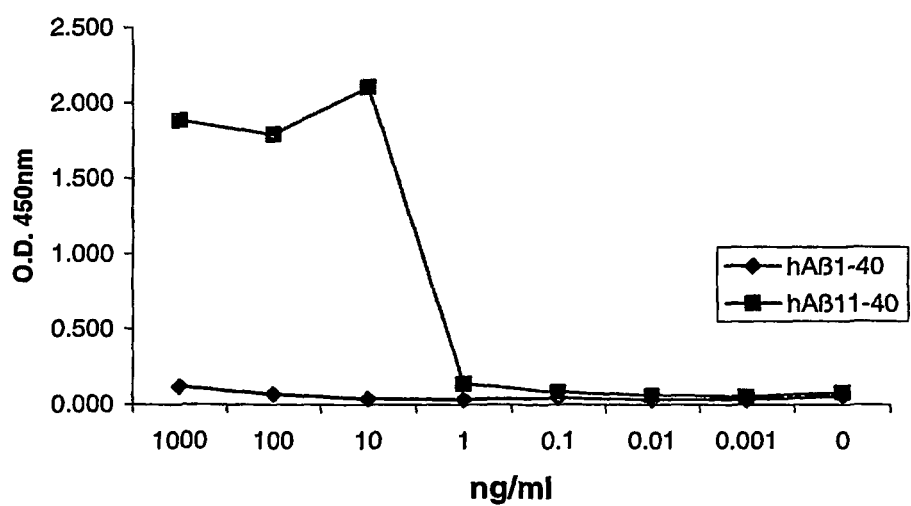

To evaluate the specificity of the antibodies, they were purified on Protein G affinity chromatography and used in a sandwich ELISA with specific anti-human cAβ40 and cAβ42 mAbs. JRF/AβN/25 was used as a specific monoclonal antibody for Aβ1-40 in combination with JRF/cAβ40/10-HRPO as detecting antibody. The latter specifically recognizes the C-terminal part of Aβ and can accordingly be used as detecting antibody both with JRF/AβN/25 and J&JPRD/hAβ11/1 and J&JPRD/hAβ11/2 the antibodies specific for the Aβ11-x peptides. FIG. 2A confirms that JRF/AβN/25 specifically reacts with Aβ1-40 without crossreactivity to Aβ11-40. From FIGS. 2B and 2C it can be seen that the antibodies J&JPRD/hAβ11/1 and J&JPRD/hAβ11/2 specifically recognize hAβ11-40 without cross reaction to human Aβ1-40.

The capability of the antibodies according to the invention to specifically label the Aβ11-x peptides in a biological sample was demonstrated in a Western blot on a membrane extract of HEK cells stably transfected with human APP and human BACE1 (FIG. 3) as well on brain slices in amyloid plaques of AD patients (Table 3). Accordingly, the use of these antibodies in combination with specific anti-human cAβ40 and anti-human cAβ42 monoclonal antibodies in sandwich ELISA's, yield sensitive assays to detect specifically human Aβ11-x peptides in different biological samples, including biological fluids and brain homogenates.

REFERENCES

1. Jarrett, J. T., Berger, E. P., Lansbury, P. T., The carboxy terminus of the beta amyloid protein is critical for the seeding of amyloid formation: implications for the pathogenesis of Alzheimer's disease. Biochem. 32 (1993) 4693-4697.
2. Selkoe, D J., Alzheimer's disease: genes, proteins, and therapy. Physiol. Rev. 81 (2001):741-766
3. Gouras, G. K., Xu, H., Jovanovic, J. N., Buxbaum, J. D., Wang, R., Relkin, N. R., Gandy, S., Generation and regulation of beta-amyloid peptide variants by neurons, J. Neurochem., 71 (1998) 1920-1925.
4. Wang, R., Sweeney, D., Gandy, S. E., Sisodia, S. S., The profile of soluble amyloid beta protein in cultured cell media. Detection and quantification of amyloid beta protein and variants by immunoprecipitation-mass spectrometry, J. Biol. Chem., 271 (1996) 31894-31902.
5. Vandermeeren, M., Geraerts, M., Pype, S., Dillen, L., Van Hove, C., Mercken, M., The functional inhibitor DAPT prevents production of amyloid β 1-34 in human and murine cell lines. Neurosci. Lett. 315 (2001) 145-148.
6. Naslund, J., Schierhorn, A., Hellman, U., Lannfelt, L., Roses A. D, Tjernberg, L. O., Silberring, J., Gandy, S. E., Winblad, B., Greengard, P., Nordstedt, C., Terenius, L., Relative abundance of Alzheimer A beta amyloid peptide variants in Alzheimer disease and normal aging, Proc. Natl. Acad. Sci. U.S.A., 91 (1994) 8378-8382.
7. Iwatsubo, T., Saido, T. C., Mann D. M., Lee, V. M.-Y., Trojanowski, J. Q. Full-length amyloid-beta (1-42(43)) and amino-terminally modified and truncated amyloid-beta 42(43) deposit in diffuse plaques. Am. J. Pathol. 149 (1996) 1823-1830.
8. Kohler, G., Howe, S. C., Milstein, C., Fusion between immunoglobulin-secreting and nonsecreting myeloma cell lines. Eur J Immunol 6 (1976) 292-295.
9. Pype, S., Moechars, D., Dillen, L., Mercken, M., Characterization of amyloid beta peptides from brain extracts of transgenic mice overexpressing the London mutant of human amyloid precursor protein, J. Neurochem. 84(3) 602-609.

TABLE 1

| Immunisation/ bleeding | Date | Mouse | Injected | |
|---|---|---|---|---|
| Priming | Jan. 23, 2002 | 1 | 100 µg | |
|  | Jan. 23, 2002 | 2 | 100 µg | |
|  | Jan. 23, 2002 | 3 | 100 µg | |
| Boost 1 | Feb. 06, 2002 | 1 | 100 µg | |
|  | Feb. 06, 2002 | 2 | 100 µg | |
|  | Feb. 06, 2002 | 3 | 100 µg | |
| Bleeding 1 | Feb. 20, 2002 | 1 | | |
|  | Feb. 20, 2002 | 2 | | |
|  | Feb. 20, 2002 | 3 | | |
| Boost 2 | Feb. 27, 2002 | 1 | 100 µg | |
|  | Feb. 27, 2002 | 2 | 100 µg | |
|  | Feb. 27, 2002 | 3 | 100 µg | |
| Bleeding 2 | Mar. 08, 2002 | 1 | | |
|  | Mar. 08, 2002 | 2 | | |
|  | Mar. 08, 2002 | 3 | | |
| Final boost | Mar. 11, 2002 | 1 | 100 µg | Mouse with ascites ! |
|  | Mar. 11, 2002 | 2 | 100 µg | Mouse with ascites ! |
|  | Mar. 11, 2002 | 3 | 100 µg | No ascites, no titer ! |
| Spleen frozen | Mouse | Date | | Spleen Cells |
| hAβ__11(6aa).10exp6 cellen | 2 | Mar. 14, 2002 | | 105.10exp6/vial (4 vials) |
| FUSION | Mouse | DATE | | Spleen Cells |
| hAβ__11(6aa) 30 pl. | 1 | Mar. 15, 2002 | | 655.10exp6 |
|  |  |  |  | 2 fusions with each 325 * $10^6$ spleencells |

TABLE 3

| | | Hippocampus | | | | Choroid plexus |
|---|---|---|---|---|---|---|
| Ab type | dilution | neurons | plagues | blood vessels | other | |
| J&JPRD/hAβ11/1 | 1 μg | − | + | − | −fissura++ −white matter++whith patchy pattern and diffuse staining | +++ |
| J&JPRD/hAβ11/1 | 5 μg | + | + | − | −fissura++ −white matter++whith patchy pattern and diffues staining | +++ |
| J&JPRD/hAβ11/2 | 1 μg | − | − | − | −fissura++ −white matter++ whith patchy pattern and diffuse staining | +++ |
| J&JPRD/hAβ11/2 | 5 μg | − | + | − | −fissural:+++ +patchy pattern in white matter | +++ |

| | | Cortex (Entorhinal or in fusiform gyrus) | | | |
|---|---|---|---|---|---|
| Ab type | dilution | neurons | n plagues | intensity | white matter |
| J&JPRD/hAβ11/1 | 1 μg | − | ++ | + | ++(patchy) |
| J&JPRD/hAβ11/1 | 5 μg | + | +++ | ++ | ++(patchy) |
| J&JPRD/hAβ11/2 | 1 μg | − | ++ | + | +++(patchy) |
| J&JPRD/hAβ11/2 | 5 μg | − | +++ | ++ | +++(patchy) |

What is claimed is:

1. A monoclonal antibody which specifically binds to a Aβ11-x polypeptide at one or more epitopes present on the first 5 to 7 N-terminal amino acids, wherein said antibody does not specifically bind to a full length Aβ1-40/42 peptide, and wherein the monoclonal antibody is produced by the hybridoma cell with the accession number LMBP 5896CB.

2. A monoclonal antibody which specifically binds to a Aβ11-x polypeptide at one or more epitopes present on the first 5 to 7 N-terminal amino acids, wherein said antibody does not specifically bind to a full length Aβ1-40/42 peptide, and wherein the monoclonal antibody is produced by the hybridoma cell with the accession number LMBP 5897CB.

3. A hybridoma which produces a monoclonal antibody which specifically binds to a Aβ11-x polypeptide at one or more epitopes present on the first 5 to 7 N-terminal amino acids, wherein said antibody does not specifically bind to a full length Aβ1-40/42 peptide, wherein the hybridoma has the accession number LMBP 5896CB.

4. A hybridoma which produces a monoclonal antibody which specifically binds to a Aβ11-x polypeptide at one or more epitopes present on the first 5 to 7 N-terminal amino acids, wherein said antibody does not specifically bind to a full length Aβ1-40/42 peptide, wherein the hybridoma has the accession number LMBP 5897CB.

* * * * *

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Immunogen consisting of the first 5 amino acids
      of the BACE1 cleavage site of human amyloid beta

<400> SEQUENCE: 1

Glu Val His His Gln
1               5

<210> SEQ ID NO 2
<211> LENGTH: 7
<212> TYPE: PRT
<213> ORGANISM: Artificial Sequence
<220> FEATURE:
<223> OTHER INFORMATION: Immunogen consisting of the first 7 amino acids
      of the BACE1 cleavage site of human amyloid beta

<400> SEQUENCE: 2

Glu Val His His Gln Lys Ile
1               5

<210> SEQ ID NO 3
<211> LENGTH: 5
<212> TYPE: PRT
<213> ORGANISM: Artificial Sequence
<220> FEATURE:
<223> OTHER INFORMATION: Immunogen consisting of the first 5 amino acids
      of the BACE1 cleavage site of mouse amyloid beta

<400> SEQUENCE: 3

Glu Val Arg His Gln
1               5

<210> SEQ ID NO 4
<211> LENGTH: 7
<212> TYPE: PRT
<213> ORGANISM: Artificial Sequence
<220> FEATURE:
```

<223> OTHER INFORMATION: Immunogen consisting of the first 7 amino acids
      of the BACE1 cleavage site of mouse amyloid beta

<400> SEQUENCE: 4

Glu Val Arg His Gln Lys Leu
1               5

<210> SEQ ID NO 5
<211> LENGTH: 136
<212> TYPE: PRT
<213> ORGANISM: Mus sp.
<220> FEATURE:
<221> NAME/KEY: CDR1
<222> LOCATION: (50)..(54)
<223> OTHER INFORMATION:
<220> FEATURE:
<221> NAME/KEY: CDR2
<222> LOCATION: (69)..(85)
<223> OTHER INFORMATION:
<220> FEATURE:
<221> NAME/KEY: CDR3
<222> LOCATION: (118)..(125)
<223> OTHER INFORMATION:

<400> SEQUENCE: 5

Met Lys Cys Ser Trp Val Ile Phe Phe Leu Met Ala Val Val Ile Gly
1               5                   10                  15

Ile Asn Ser Glu Gly Gln Leu Gln Gln Ser Gly Ala Glu Leu Val Arg
            20                  25                  30

Ser Gly Ala Ser Leu Lys Leu Ser Cys Thr Ala Ser Gly Phe Asn Ile
        35                  40                  45

Lys Asp His Tyr Val His Trp Val Arg Gln Arg Pro Glu Gln Gly Leu
    50                  55                  60

Asp Trp Ile Gly Trp Ile Ala Pro Lys Asn Gly Tyr Ser Glu Ser Ala
65                  70                  75                  80

Pro Lys Phe Gln Gly Lys Ala Ser Met Thr Ala Asp Thr Ser Ser Asn
                85                  90                  95

Thr Val Tyr Leu Gln Leu Ser Ser Leu Thr Ser Glu Asp Thr Ala Val
            100                 105                 110

Tyr Tyr Cys Phe Ala Gly Phe Tyr Asp Ser Ser Leu Tyr Trp Gly Gln
        115                 120                 125

Gly Thr Thr Leu Thr Val Ser Ser
    130                 135

<210> SEQ ID NO 6
<211> LENGTH: 133
<212> TYPE: PRT
<213> ORGANISM: Mus sp.
<220> FEATURE:
<221> NAME/KEY: CDR1
<222> LOCATION: (44)..(59)
<223> OTHER INFORMATION:
<220> FEATURE:
<221> NAME/KEY: CDR2
<222> LOCATION: (75)..(81)
<223> OTHER INFORMATION:
<220> FEATURE:
<221> NAME/KEY: CDR3
<222> LOCATION: (114)..(122)
<223> OTHER INFORMATION:

<400> SEQUENCE: 6

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ala

-continued

```
                    20                  25                  30
Val Thr Ile Gly Gln Pro Ala Ser Ile Ser Cys Lys Ser Gly Gln Ser
                35                  40                  45

Leu Leu Ala Arg Asp Gly Lys Thr Tyr Leu Ser Trp Leu Leu Gln Arg
         50                  55                  60

Pro Gly Gln Ser Pro Lys Arg Leu Ile Tyr Leu Val Ser Lys Leu Asp
 65                  70                  75                  80

Ser Gly Val Pro Asp Arg Phe Ser Gly Ser Gly Ser Gly Thr Asp Phe
                 85                  90                  95

Thr Leu Lys Ile Asn Arg Val Glu Ala Glu Asp Leu Gly Val Tyr Tyr
            100                 105                 110

Cys Trp Gln Gly Thr His Phe Pro Arg Thr Phe Gly Gly Gly Thr Asn
            115                 120                 125

Leu Glu Ile Lys Arg
        130

<210> SEQ ID NO 7
<211> LENGTH: 133
<212> TYPE: PRT
<213> ORGANISM: Mus sp.
<220> FEATURE:
<221> NAME/KEY: CDR1
<222> LOCATION: (50)..(54)
<223> OTHER INFORMATION:
<220> FEATURE:
<221> NAME/KEY: CDR2
<222> LOCATION: (69)..(85)
<223> OTHER INFORMATION:
<220> FEATURE:
<221> NAME/KEY: CDR3
<222> LOCATION: (118)..(122)
<223> OTHER INFORMATION:

<400> SEQUENCE: 7

Met Gly Trp Ser Trp Ile Phe Leu Phe Leu Leu Ser Gly Thr Ala Gly
 1               5                  10                  15

Val Leu Ser Glu Val Gln Leu Gln Gln Ser Gly Pro Asp Leu Val Lys
                20                  25                  30

Pro Gly Ala Ser Val Lys Thr Ser Cys Lys Thr Ser Gly Tyr Ser Phe
            35                  40                  45

Thr Glu Tyr Ile Met Ser Trp Val Arg Gln Ser His Gly Lys Ser Leu
     50                  55                  60

Glu Trp Ile Gly Ser Ile Asn Pro Asn Thr Gly Gly Ser Arg Tyr Asn
 65                  70                  75                  80

Gln Lys Phe Lys Gly Lys Ala Thr Leu Thr Val Asp Lys Ser Ser Ser
                 85                  90                  95

Thr Ala Tyr Met Glu Phe Arg Ser Leu Thr Ser Glu Asp Ser Ala Val
            100                 105                 110

Tyr Tyr Cys Ala Arg Gly Asp Phe Asp Tyr Trp Gly Gln Gly Thr Thr
            115                 120                 125

Leu Thr Val Ser Ser
        130

<210> SEQ ID NO 8
<211> LENGTH: 133
<212> TYPE: PRT
<213> ORGANISM: Mus sp.
<220> FEATURE:
<221> NAME/KEY: CDR1
<222> LOCATION: (44)..(59)
<223> OTHER INFORMATION:
```

```
<220> FEATURE:
<221> NAME/KEY: CDR2
<222> LOCATION: (75)..(81)
<223> OTHER INFORMATION:
<220> FEATURE:
<221> NAME/KEY: CDR3
<222> LOCATION: (114)..(122)
<223> OTHER INFORMATION:

<400> SEQUENCE: 8

Met Arg Phe Ser Ala Gln Leu Leu Gly Leu Val Leu Trp Ile Pro
 1               5                  10                  15

Gly Ser Thr Ala Asp Ile Val Met Thr Gln Ala Ala Phe Ser Asn Pro
                20                  25                  30

Val Thr Leu Gly Thr Ser Ala Ser Ile Ser Cys Arg Ser Lys Asn
                35                  40                  45

Leu Leu His Ser Asn Gly Ile Thr Tyr Leu Tyr Trp Tyr Leu Gln Arg
            50                  55                  60

Pro Gly Gln Ser Pro Gln Leu Leu Ile Ser Arg Val Ser Asn Leu Ala
 65                  70                  75                  80

Ser Gly Val Pro Asn Arg Phe Ser Gly Ser Glu Ser Gly Thr Asp Phe
                    85                  90                  95

Thr Leu Arg Ile Ser Arg Val Glu Ala Glu Asp Val Gly Val Tyr Tyr
                100                 105                 110

Cys Ala Gln Leu Leu Glu Leu Pro Phe Thr Phe Gly Ser Gly Thr Lys
                115                 120                 125

Leu Glu Ile Lys Arg
            130

<210> SEQ ID NO 9
<211> LENGTH: 138
<212> TYPE: PRT
<213> ORGANISM: Mus sp.
<220> FEATURE:
<221> NAME/KEY: CDR1
<222> LOCATION: (50)..(54)
<223> OTHER INFORMATION:
<220> FEATURE:
<221> NAME/KEY: CDR2
<222> LOCATION: (69)..(85)
<223> OTHER INFORMATION:
<220> FEATURE:
<221> NAME/KEY: CDR3
<222> LOCATION: (118)..(127)
<223> OTHER INFORMATION:

<400> SEQUENCE: 9

Met Glu Trp Thr Trp Val Phe Leu Phe Leu Leu Ser Val Thr Ala Gly
 1               5                  10                  15

Val His Ser Gln Val Gln Leu Gln Gln Ser Gly Pro Glu Leu Met Lys
                20                  25                  30

Pro Gly Ala Ser Val Lys Ile Ser Cys Lys Ala Thr Gly Tyr Thr Phe
            35                  40                  45

Ser Thr Ser Trp Ile Glu Trp Ile Lys Gln Arg Pro Gly His Gly Leu
 50                  55                  60

Glu Trp Ile Gly Glu Val Leu Pro Gly Ser Gly Lys Ser Asn His Asn
 65                  70                  75                  80

Ala Asn Phe Lys Gly Arg Ala Thr Phe Thr Ala Asp Thr Ala Ser Asn
                85                  90                  95

Thr Ala Tyr Met Gln Leu Ser Ser Leu Thr Ser Glu Asp Ser Ala Val
                100                 105                 110
```

```
Tyr Tyr Cys Ala Arg Glu Gly Ser Asn Asn Ala Leu Ala Tyr Trp
            115                 120                 125

Gly Gln Gly Thr Leu Val Thr Val Ser Ala
        130                 135

<210> SEQ ID NO 10
<211> LENGTH: 128
<212> TYPE: PRT
<213> ORGANISM: Mus sp.
<220> FEATURE:
<221> NAME/KEY: CDR1
<222> LOCATION: (46)..(55)
<223> OTHER INFORMATION:
<220> FEATURE:
<221> NAME/KEY: CDR2
<222> LOCATION: (60)..(67)
<223> OTHER INFORMATION:
<220> FEATURE:
<221> NAME/KEY: CDR3
<222> LOCATION: (110)..(117)
<223> OTHER INFORMATION:

<400> SEQUENCE: 10

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Tyr Met His Trp Tyr Gln Gln Lys Ser Gly Thr Ser
    50                  55                  60

Pro Lys Arg Trp Ile Tyr Asp Ser Ser Arg Leu Ala Ser Gly Val Pro
65                  70                  75                  80

Ser Arg Phe Ser Gly Gly Ser Gly Thr Ser Tyr Ser Pro Thr Ile
                85                  90                  95

Ser Asn Met Glu Ala Glu Asp Ala Ala Thr Tyr Phe Cys Gln Asn Trp
            100                 105                 110

Arg Ser Ser Pro Thr Phe Gly Ala Gly Thr Lys Leu Glu Leu Lys Arg
        115                 120                 125

<210> SEQ ID NO 11
<211> LENGTH: 133
<212> TYPE: PRT
<213> ORGANISM: Mus musculus
<220> FEATURE:
<221> NAME/KEY: CDR1
<222> LOCATION: (50)..(54)
<223> OTHER INFORMATION:
<220> FEATURE:
<221> NAME/KEY: CDR2
<222> LOCATION: (69)..(85)
<223> OTHER INFORMATION:
<220> FEATURE:
<221> NAME/KEY: CDR3
<222> LOCATION: (118)..(122)
<223> OTHER INFORMATION:

<400> SEQUENCE: 11

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Asp Leu Val Lys
            20                  25                  30

Pro Gly Ala Ser Val Lys Thr Ser Cys Lys Thr Ser Gly Tyr Ser Phe
        35                  40                  45
```

```
Thr Glu Tyr Ile Met Ser Trp Val Arg Gln Ser His Gly Lys Ser Leu
    50                  55                  60

Glu Trp Ile Gly Ser Ile Asn Pro Asn Thr Gly Gly Ser Arg Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Phe Arg Ser Leu Thr Ser Glu Asp Ser Ala Val
                100                 105                 110

Tyr Tyr Cys Ala Arg Gly Asp Phe Asp Tyr Trp Gly Gln Gly Thr Thr
            115                 120                 125

Leu Thr Val Ser Ser
    130

<210> SEQ ID NO 12
<211> LENGTH: 133
<212> TYPE: PRT
<213> ORGANISM: Mus musculus
<220> FEATURE:
<221> NAME/KEY: CDR1
<222> LOCATION: (44)..(59)
<223> OTHER INFORMATION:
<220> FEATURE:
<221> NAME/KEY: CDR2
<222> LOCATION: (75)..(81)
<223> OTHER INFORMATION:
<220> FEATURE:
<221> NAME/KEY: CDR3
<222> LOCATION: (114)..(122)
<223> OTHER INFORMATION:

<400> SEQUENCE: 12

Met Arg Phe Ser Ala Gln Leu Leu Gly Leu Leu Val Leu Trp Ile Pro
1               5                   10                  15

Gly Ser Thr Ala Asp Ile Val Met Thr Gln Ala Ala Phe Ser Asn Pro
                20                  25                  30

Val Thr Leu Gly Thr Ser Ala Ser Ile Ser Cys Arg Ser Ser Lys Asn
            35                  40                  45

Leu Leu His Ser Asn Gly Ile Thr Tyr Leu Tyr Trp Tyr Leu Gln Arg
    50                  55                  60

Pro Gly Gln Ser Pro Gln Leu Leu Ile Ser Arg Val Ser Asn Leu Ala
65                  70                  75                  80

Ser Gly Val Pro Asn Arg Phe Ser Gly Ser Glu Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Leu Leu Glu Leu Pro Phe Thr Phe Gly Ser Gly Thr Lys
            115                 120                 125

Leu Glu Ile Lys Arg
    130
```